United States Patent [19]

Maas et al.

[11] Patent Number: 5,104,861
[45] Date of Patent: Apr. 14, 1992

[54] 7-OXOPROSTACYCLIN DERIVATIVES WHICH ARE USEFUL AS PHARMACEUTICALS

[75] Inventors: Manfred Maas, Kirchberg an der Murr; Helmut Vorbruggen; Claus-Steffen Sturzebecher, both of Berlin, all of Fed. Rep. of Germany

[73] Assignee: Schering Aktiengesellschaft, Berlin and Bergkamen, Fed. Rep. of Germany

[21] Appl. No.: 657,965

[22] PCT Filed: Mar. 25, 1987

[86] PCT No.: PCT/DE87/00132
§ 371 Date: Feb. 2, 1988
§ 102(e) Date: Feb. 2, 1988

[87] PCT Pub. No.: WO87/05900
PCT Pub. Date: Oct. 8, 1987

Related U.S. Application Data

[63] Continuation of Ser. No. 146,780, Feb. 2, 1988, abandoned.

[30] Foreign Application Priority Data

Mar. 26, 1986 [DE] Fed. Rep. of Germany ....... 3610556

[51] Int. Cl.$^5$ ............... A61K 31/557; C07D 307/937
[52] U.S. Cl. .................................. 514/63; 514/460; 514/470; 549/214; 549/415; 549/465
[58] Field of Search ............... 549/465, 214, 415; 514/470, 63, 460

[56] References Cited

U.S. PATENT DOCUMENTS

| 3,923,861 | 12/1975 | Nelson ..................... 549/312 |
| 4,330,553 | 5/1982 | Simonidesz et al. ........... 549/465 |
| 4,466,969 | 8/1984 | Nickolson et al. ............ 549/465 |
| 4,499,293 | 2/1985 | Johnson et al. .............. 549/465 |
| 4,687,864 | 8/1987 | Djuric et al. ............... 549/465 |

FOREIGN PATENT DOCUMENTS

0119949 9/1984 European Pat. Off. .
85/02187 5/1985 World Int. Prop. O. .

OTHER PUBLICATIONS

Bindra et al., Prostaglandin Synthesis, Academic Press, N.Y., pp. 453, 460, 461, 471 (1977).
Skerballa et al. I, Adv. in Prostaglandin Thromboxane, Leukotriene Research, vol. 15 (Raven Press), pp. 271-273 (1985).

Primary Examiner—Bernard Dentz
Attorney, Agent, or Firm—Millen, White & Zelano

[57] ABSTRACT

The invention relates to 7-oxoprostacyclin derivatives of Formula I

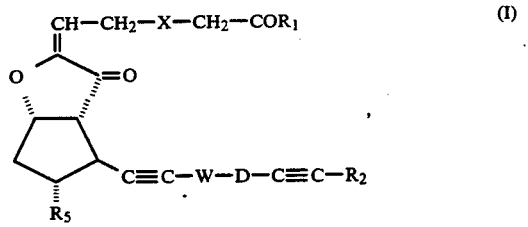

wherein
$R_1$ is the residue $OR_3$ wherein $R_3$ can mean hydrogen or alkyl of 1-10 carbon atoms optionally substituted by halogen, phenyl, $C_1$-$C_4$-alkoxy or $C_1$-$C_4$-dialkylamino, or the residue $NHR_4$ meaning an alkanoyl or alkanesulfonyl residue of respectively 1-10 carbon atoms,
W is a hydroxymethylene or a

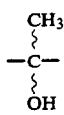

group wherein the OH-group can be respectively esterified with a benzoyl or alkanoic acid residue of 1-4 carbon atoms or etherified with a tetrahydropyranyl, tetrahydrofuranyl, ($C_1$-$C_4$-alkoxy)-$C_1$-$C_4$-alkyl or tri-($C_1$-$C_4$-alkyl)-silyl residue, wherein the free or modified OH-group can be in the α- or β-position,
D is a straight-chain or branched alkylene group of 1-5 carbon atoms,
$R_2$ is a straight-chain or branched alkyl group of 1-6 carbon atoms,
$R_5$ is a hydroxy group which can be esterified with an alkanoic acid residue of 1-4 carbon atoms or etherified with a tetrahydropyranyl, tetrahydrofuranyl, ($C_1$-$C_4$-alkoxy)-$C_1$-$C_4$-alkyl or tri-($C_1$-$C_4$-alkyl)silyl residue,
X is an oxygen atom or the residue —$CH_2$—, and, if $R_3$ means hydrogen, the salts thereof
with physiologically compatible bases, to processes for their preparation, and to their use as medicinal agents.

8 Claims, No Drawings

7-OXOPROSTACYCLIN DERIVATIVES WHICH ARE USEFUL AS PHARMACEUTICALS

This application is a continuation of application Ser. No. 07/146,780, filed Feb. 2, 1988 now abandoned.

The invention relates to novel prostacyclin derivatives, processes for their preparation, as well as their use as medicinal agents.

European Patent EP 59,756 discloses 7-oxoprostacyclins exhibiting blood-pressure-lowering, bronchodilatory, and thrombocyte-aggregation-inhibiting properties.

It has now been found that the introduction of a 3-oxa group and an acetylene group in the 13,14-position results in stabilization of the prostacyclin molecule, the pharmacological spectrum of efficacy being preserved and the duration of effectiveness of the novel prostacyclins being markedly prolonged.

The compounds of this invention exhibit antihypertensive activity. They are furthermore suitable for inhibition of thrombocyte aggregation, of vasodilation, and of gastric acid secretion.

The advantage of the compounds of this invention resides in their dissociation of activity. They have a similarly antihypertensive effect as iloprost, but do not inhibit thrombocyte aggregation as strongly as iloprost.

The invention concerns 7-oxoprostacyclins of Formula I

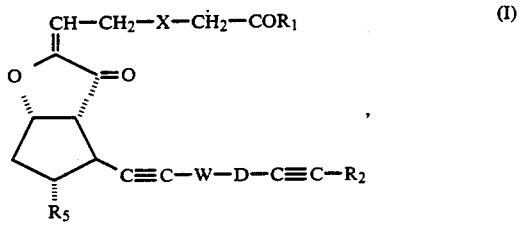

wherein
$R_1$ is the residue $OR_3$ wherein $R_3$ can mean hydrogen or alkyl of 1-10 carbon atoms optionally substituted by halogen, phenyl, $C_1$-$C_4$-alkoxy or $C_1$-$C_4$-dialkylamino, or the residue $NHR_4$ with $R_4$ meaning TM an alkanoyl or alkanesulfonyl residue of respectively 1-10 carbon atoms,
W is a hydroxymethylene or a

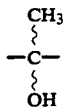

wherein the OH-group can be respectively esterified with a benzoyl or alkanoic acid residue of 1-4 carbon atoms or etherified with a tetrahydropyranyl, tetrahydrofuranyl, ($C_1$-$C_4$-alkoxy)-$C_1$-$C_4$-alkyl or tri-($C_1$-$C_4$-alkyl)silyl residue, wherein the free or modified OH-group can be in the α- or β-position,
D is a straight-chain or branched alkylene group of 1-5 carbon atoms,
$R_2$ is a straight-chain or branched alkyl group of 1-6 carbon atoms,
$R_5$ is a hydroxy group which can be esterified with an alkanoic acid residue of 1-4 carbon atoms or etherified with a tetrahydropyranyl, tetrahydrofuranyl, ($C_1$-$C_4$alkoxy-$C_1$-$C_4$-alkyl or tri-($C_1$-$C_4$-alkyl)silyl residue,
X is an oxygen atom or the residue $-CH_2-$, and, if $R_3$ means hydrogen, the salts thereof with physiologically compatible bases.

The alkyl group $R_3$ can be considered to be straight or branched alkyl groups of 1-10 carbon atoms such as, for example, methyl, ethyl, propyl, butyl, isobutyl, tert-butyl, pentyl, neopentyl, heptyl, hexyl, decyl. The alkyl groups $R_3$ can optionally be mono- to polysubstituted by halogen atoms, alkoxy groups of 1-4 carbon atoms, and dialkylamines of 1-4 carbon atoms. Alkyl groups which are monosubstituted are preferred. Examples for substituents are fluorine, chlorine or bromine atoms, phenyl, dimethylamine, methoxy, ethoxy. Preferred alkyl groups $R_3$ that can be cited are those of 1-4 carbon atoms, such as, for example, methyl, ethyl, propyl, dimethylaminopropyl, isobutyl and butyl.

Physiologically compatible acid resides are suitable as the acid residue $R_4$. Preferred acids are organic carboxylic acids and sulfonic acids of 1-15 carbon atoms pertaining to the aliphatic, cycloaliphatic, aromatic, aromatic-aliphatic and heterocyclic series. These acids can be saturated, unsaturated and/or polybasic and/or substituted in the usual way. Examples for the substituents are alkyl, hydroxy, alkoxy, oxo or amino groups or halogen atoms.

The following carboxylic acids can be cited, for example: formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, cyclopropylacetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di- and trichloroacetic acid, aminoacetic acid, diethylaminoacetic acid, piperidinoacetic acid, morpholinoacetic acid, lactic acid, succinic acid, adipic acid, benzoic acid, benzoic acids substituted by halogen, trifluoromethyl, hdyroxy, alkoxy or carboxy groups, nicotinic acid, isonicotinic acid, furan-2-carboxylic acid, cyclopentylpropionic acid. Especially preferred acyl residues are considered to be those of up to 10 carbon atoms.

Sulfonic acids of up to 10 carbon atoms are, for example, methanesulfonic acid, ethanesulfonic acid, isopropanesulfonic acid, β-chloroethanesulfonic acid, butanesulfonic acid, cyclopentanesulfonic acid, cyclohexanesulfonic acid, benzenesulfonic acid, p-toluenesulfonic acid, p-chlorobenzenesulfonic acid, N,N-dimethylaminosulfonic acid, N,N-diethylaminosulfonic acid, N,N-bis(β-chloroethyl)aminosulfonic acid, N,N-diisobutylaminosulfonic acid, N,N-dibutylaminosulfonic acid, pyrrolidino-, piperidino-, piperazino-, N-methylpiperazino- and morpholinosulfonic acid.

The hydroxy groups $R_5$ and those in W can be functionally modified, for example by etherification or esterification wherein the free or modified hydroxy groups in W can be in the α- or β-position, and wherein free hydroxy groups are preferred. Suitable ether, and acyl residues are the residues known to a person skilled in the art. Readily cleavable ether residues are preferred, such as, for example, the tetrahydropyranyl, tetrahydrofuranyl, α-ethoxyethyl, trimethylsilyl, dimethyltert-butylsilyl and tribenzylsilyl residues. Suitable acyl residues are $C_1$–$C_4$-alkanoyl residues, such as, for example, acetyl, propionyl, butyryl or benzoyl.

Suitable alkyl groups $R_2$ are straight- or branched-chain alkyl residues of 1–10, especially 1–6 carbon atoms. Examples that can be cited are methyl, ethyl, propyl, butyl, isobutyl, tert-butyl, pentyl, hexyl, heptyl, octyl.

Alkylene groups D can be straight-chain or branched-chain alkylene residues of 1–10, especially 1–5 carbon atoms. Examples are: methylene, ethylene, 1,2-propylene, ethylethylene, trimethylene, tetramethylene, pentamethylene, 1-methyltetramethylene, 1-methyltrimethylene, 2-methyltrimethylene, 2-methyltetramethylene.

Inorganic and organic bases are suitable for the salt formation with the free acids ($R_3$=H), as known to those skilled in the art for the formation of physiologically compatible salts.

Examples that can be cited are: alkali hydroxides, such as sodium and potassium hydroxide, alkaline earth hydroxides, such as calcium hydroxide, ammonia, amines, such as ethanolamine, diethanolamine, triethanolamine, N-methylglucamine, morpholine, tris(hydroxymethyl)methylamine, etc.

The invention furthermore relates to a process for preparing the 7-oxoprostacyclins of Formula I according to this invention, characterized by conventionally oxidizing a compound of Formula II

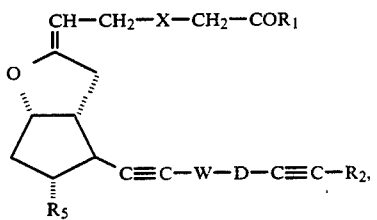

wherein $R_1$, $R_2$, $R_5$, W and D have the meanings given above, with selenium dioxide.

The reaction of the compounds of Formula II with selenium dioxide is conducted at temperatures of 20°–140° C., preferably at 50°–120° C., in an organic solvent, preferably dioxane or tert-butanol, within 0.5–10 hours under an inert gas (such as, for example, $N_2$ or Ar) and with agitation, optionally with the addition of an amine base, such as pyridine or hexamethyldisilazane.

Saponification of the 7-oxoprostacyclin esters is performed according to the methods known to persons skilled in the art, for example with alkaline catalysts. Introduction of the ester group wherein $R_3$ represents an alkyl group of 1–10 carbon atoms takes place in accordance with the methods known to those skilled in the art. The carboxy compounds are reacted, for example, with diazo hydrocarbons in a conventional process. Esterification with diazo hydrocarbons is performed, for example, by mixing a solution of the diazo hydrocarbon in an inert solvent, preferably in diethyl ether, with the carboxy compound in the same or in a different inert solvent, e.g., methylene chloride. After the reaction is finished within 1–30 minutes, the solvent is removed and the ester purified in the usual way. Diazoalkanes are either known or can be produced in accordance with known methods [Org. Reactions 8 : 389–394 (1954)].

The 7-oxoprostacyclin derivatives of general Formula I wherein $R_3$ means a hydrogen atom can be converted into salts with suitable amounts of the corresponding inorganic bases with neutralization. For example, when dissolving the corresponding PG acids in water containing the stoichiometric quantity of the base, the solid inorganic salt is obtained after evaporation of the water or after addition of a water-miscible solvent, e.g., alcohol or acetone.

In order to produce an amine salt, which is done in the usual way, the PG acid is dissolved, for example, in a suitable solvent, e.g., ethanol, acetone, acetonitrile, diethyl ether or benzene, and at least the stoichiometric amount of the amine is added to this solution. During this step, the salt is ordinarily obtained in the solid form, or it is isolated as usual after evaporation of the solvent.

The functional modification of the free OH-groups takes place according to the methods known to one skilled in the art. For introduction of the ether blocking groups, the reaction is performed, for example, with dihydropyran in methylene chloride, benzene, or chloroform with the use of an acidic catalyst, such as, for example, $POCl_3$, p-toluenesulfonic acid or anhydrous mineral acids. The dihydropyran is used in excess, preferably in two to ten times the amount required theoretically. The reaction is normally completed at 0° C. to 30° C. after 15–30 minutes.

Introduction of the acyl blocking groups takes place by conventionally reacting a compound of general Formula I with a carboxylic acid derivative, such as, for example, acid chloride, acid anhydride, and others, in the presence of a tertiary amine base, such as, e.g. pyridine, dimethylaminopyridine, etc.

Liberation of a functionally modified OH-group to obtain the compounds of Formula I is performed according to known methods. For example, the ether blocking groups are split off in an aqueous solution of an organic acid, e.g., acetic acid, propionic acid, etc., or in an aqueous solution of an inorganic acid, e.g., hydrochloric acid. To improve solubility, a water-miscible, inert organic solvent is suitably added. Organic solvents that can be used are, for example, alcohols, such as methanol and ethanol, and ethers, such as dimethoxyethane, dioxane and tetrahydrofuran. Tetrahydrofuran is employed with preference. The splitting off step is preferably performed at temperatures of between 20° C. and 80° C.

Splitting off of the silyl ether blocking groups takes place, for example, with tetrabutylammonium fluoride or with KF in the presence of a crown ether. Examples of suitable solvents are tetrahydrofuran, diethyl ether, dioxane, methylene chloride, etc. The splitting off step is preferably carried out at temperatures of between 0° C. and 80° C.

Saponification of the acyl groups takes place, for example, with alkali or alkaline earth carbonates or hydroxides in an alcohol or in the aqueous solution of an alcohol. Suitable alcohols are aliphatic alcohols, such as, for example, methanol, ethanol, butanol, etc., preferably methanol. Alkali carbonates and hydroxides that can be mentioned are potassium and sodium salts, but the potassium salts are preferred. Examples of alkaline earth carbonates and hydroxides are calcium carbonate, calcium hydroxide and barium carbonate. The reaction is conducted at −10° C. to 70° C., preferably at 25° C.

Reaction of the compound of Formula I wherein $R_3$ means a hydrogen atom with an isocyanate of the general formula $$R_4-N=C=O \qquad (V)$$

wherein R₄ has the meanings given above, is conducted optionally with the addition of a tertiary amine, such as, for example, triethylamine or pyridine. The reaction can be performed without a solvent or in an inert solvent, preferably acetonitrile, tetrahydrofuran, acetone, dimethylacetamide, methylene chloride, diethyl ether, benzene, toluene, dimethyl sulfoxide, at temperatures of above or below room temperature, e.g. between −80° C. to 100° C., preferably at 0° C. to 30° C.

The compounds of Formula II serving as the starting material can be produced, for example, by reacting conventionally a known prostaglandin F derivative of Formula III

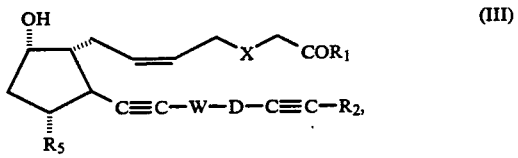

with iodine in the presence of an alkali hydrogen carbonate or alkali carbonate to obtain the compounds of general Formula IV

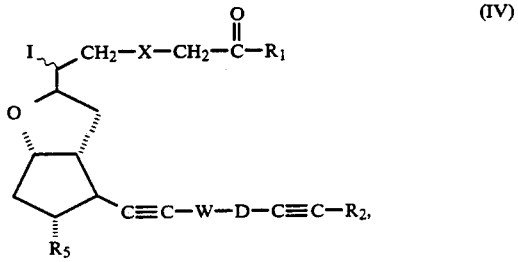

[J. Tömöskäzi et al., Tetrahedron Letters, 2627 (1977)].

Subsequently, if desired, free hydroxy groups can be blocked by esterification, etherification or silylation. Depending on the desired meaning for the residues in the final products of Formula I, it is possible optionally to esterify a carboxy group or to react a carboxy group with compounds of Formula V.

Reaction of the compounds of Formula IV to the compounds of Formula II can be performed, for example, with 1,5-diazabicyclo[3.4.0]nonene-5 (DBN) or 1,5-diazabicyclo[5.4.0]undecene-5 (DBU) in an inert solvent, such as benzene, toluene, tetrahydrofuran, etc., or with sodium methylate in methanol. The hydrogen halide is split off at temperatures of between 0° C. and 120° C., preferably at 20°-60° C.

The compounds of this invention are suitable for therapy in connection with diseases of the cardiovascular system, stomach, pancreas, liver and kidneys. They have blood-pressure-lowering and bronchodilatory activities. They are furthermore suitable for inhibiting thrombocyte aggregation. Consequently, the novel carbacyclin derivatives of Formula I represent valuable pharmaceutically active agents. Moreover, they exhibit, with a similar spectrum of activity, a higher specificity and, above all, substantially longer lasting efficacy as compared with corresponding prostaglandins and prostacyclins. As compared to $PGI_2$, they are distinguished by higher stability. The high tissue specificity of the novel carbacyclins is demonstrated in a study on smooth-muscle organs, such as, for example, on guinea pig ileum or isolated rabbit trachea where a substantially lower stimulation can be observed than in the administration of natural prostaglandins of the E-, A or F-type.

The novel prostacyclin analogs possess the properties typical for prostacyclins, such as, for example, lowering of peripheral arterial and coronary vascular resistance, inhibition of thrombocyte aggregation and dissolution of platelet thrombi, myocardial cytoprotection, lowering of systemic blood pressure without simultaneously reducing stroke volume and coronary blood flow; treatment for stroke, prophylaxis and therapy of coronary heart disease, coronary thrombosis, cardiac infarction, peripheral arterial diseases, arteriosclerosis and thrombosis, prophylaxis and therapy of ischemic attacks on the CNS system, therapy for shock, inhibition of bronchoconstriction, inhibition of gastric acid secretion and cytoprotection of gastric and intestinal mucosa; cytoprotection in the liver, in the pancreas and in the kidneys, antiallergic properties, lowering of pulmonary vascular resistance and of pulmonary pressure, promotion of renal blood flow, utilization in place of heparin or as adjuvant in dialysis or hemofiltration, preservation of stored blood and stored thrombocytes, transplants, inhibition of labor, treatment of gestational toxicosis, enhancement of cerebral blood flow, treatment of asthma, incorporation into synthetic blood vessels, surgical suture material, vein catheters, etc. Furthermore, the novel prostacyclin analogs reduce internal eye pressure and exhibit antiproliferative properties. The novel carbacyclins can additionally be utilized in combination, for example, with β-blockers, diuretics, phosphodiesterase inhibitors, Ca antagonists, t-PA, nonsteroidal anti-inflammatory agents, leukotriene synthetase inhibitors, leukotriene antagonists, thromboxane synthetase inhibitors, or thromboxyne antagonists.

The novel prostacyclins are furthermore distinguished by suppressing rejection reactions and by their antimetastatic effect. They act to keep open Botallo's duct (before operations). They are furthermore suited for treatment of diarrhea and for improving bowel movement.

The dosage of the compounds is 1-1,500 μg/kg/day if administered to human patients. The dosage unit for the pharmaceutically acceptable excipient is 0.01-100 mg.

Upon intravenous injection administered to nonanesthetized, hypertonic rats in doses of 5, 20 and 100 μg/kg body weight, the compounds of this invention show a stronger hypotensive and longer lasting effect than $PGE_2$ and $PGA_2$, without triggering diarrhea, as does $PGE_2$ or cardiac arrhythmias, as does $PGA_2$.

When injected intravenously into anesthetized rabbits, the compounds of this invention, as compared with $PGE_2$ and $PGA_2$, show a stronger and considerably longer lasting reduction in blood pressure without affecting other smooth-muscle organs or organ functions.

For parenteral administration, sterile, injectable, aqueous or oily solutions are utilized. Suitable for oral administration are, for example, tablets, dragees or capsules.

Consequently, the invention also relates to medicinal agents based on the compounds of general Formula I and conventional auxiliary agents and excipients.

The active agents of this invention are to serve, in conjunction with the auxiliary agents known and customary in galenic pharmacy, for example for the production of antihypertensives.

EXAMPLE 1

(1a)
(1S,5R,6R,7R)-6-[(E)-(4S)-2-Bromo-3-oxo-4-methyl-non-1-en-6-ynyl]-7-benzoyloxy-2-oxabicyclo[3.3.0]octan-3-one At 0° C., a solution of 3.05 g of dimethyl-(2-oxo-3β-methyloct-5-ynyl)phosphonate in 30 ml of anhydrous dimethoxyethane is added dropwise to a suspension of 575 mg of sodium hydride/paraffin oil suspension (50/50) in 50 ml of dimethoxyethane. After the release of gas has ceased, the mixture is stirred under cooling for 30 minutes. Then, 2.205 g of finely pulverized N-bromosuccinimide is added and agitation is continued for another hour at 0° to +5° C. Subsequently, the mixture is combined with a solution of 2.74 g of Corey lactone in 35 ml of dimethoxyethane and stirred for another 2 hours under cooling. Then the mixture is poured into 1 liter of ice-cold 10% strength ammonium chloride solution and extracted three times with ether. The extract is washed twice with water, dried with magnesium sulfate, and, after filtration, freed of solvent under vacuum. The crude product is purified by chromatography on silica gel with a hexane-ethyl acetate gradient system, thus obtaining 3.01 g of the above compound = 64% of theory.

IR: 1760 cm$^{-1}$ (3-one), 1720 cm$^{-1}$ (7-benzoate), 1700 cm$^{-1}$ (3-oxo)

(1b)
(1S,5S,6R,7R)-6-[(E)-(3RS,4S)-2-Bromo-3-hydroxy-4-methylnon-1-en-6-ynyl]-7-benzoyloxy-2-oxabicyclo[3.3.0]octan-3-one At −40° C., 1.444 g of sodium borohydride is added in portions to a solution of 3.01 g of the ketone produced according to the above example in 76 ml of anhydrous methanol. After 80 minutes, 1.91 ml of glacial acetic acid is added gently dropwise. The mixture is diluted with water and extracted three times with ether. The extract is washed once with ice-cold sodium bicarbonate solution and twice with water. After drying over magnesium sulfate and filtration, the mixture is evaporated under vacuum. The 3-hydroxy mixture is separated into the epimers by chromatography on silica gel with a pentane/ether gradient system, thus obtaining 23-30% of theory of the desired S epimer and 60-63% of the R compound. By reoxidation of the latter with Jones reagent and repeated reduction, the yield of S compound can be raised to 61% of theory.

IR: 3480 cm$^{-1}$ (3-hydroxy), 1760 cm$^{-1}$ (3-one), 1720 cm$^{-1}$ (7-benzoate), 1665 cm$^{-1}$ ($\Delta^{1,2}$)

(1c)
(1S,5R,6R,7R)-6-[(E)-(3S,4S)-2-Bromo-3-hydroxy-4-methylnon-1-en-6-ynyl]-7-hydroxy-2-oxabicyclo[3.3.0]octan-3-one 1.10 g of the 3S isomer of the above example is dissolved in 9.2 ml of anhydrous methyl alcohol, 160 mg of anhydrous potassium carbonate is added, and the mixture is stirred under argon and exclusion of moisture for 3 hours at room temperature. After cooling to ice bath temperature, the mixture is neutralized by adding 0.16 ml of 37% strength hydrochloric acid. Then the methyl alcohol is distilled off under vacuum at maximally 30°. The residue is combined with dichloromethane, dried with magnesium sulfate. The residue remaining after filtering off the drying agent and removal of the solvent is purified by chromatography on silica gel with a hexane-acetone system. The yield is 775 mg = 90% of theory.

IR: 3350 cm$^{-1}$ (OH), 1760 cm$^{-1}$ (3-one)

(1d)
(1S,5R,6R,7R)-6-[(E)-(3S,4S)-2-Bromo-3-tetrahydropyran-2-yloxy)-4-methylnon-1-en-6-ynyl]-7-(tetrahydropyran-2-yloxy)-2-oxabicyclo[3.3.0]-octan-3-one 754 mg of the diol from the above example is dissolved in 13.8 ml of dry dichloromethane, 0.45 ml of dihydropyran and 3 mg of p-toluenesulfonic acid are added, and the mixture is stirred at room temperature for 90 minutes. By adding several drops of triethylamine, the acid is then neutralized. The solution is washed three times with water, dried with magnesium sulfate and freed of solvent under vacuum after filtration. The residue is purified by chromatography on silica gel with a hexane/ethyl acetate system, thus obtaining 1.01 g in correspondence with 92% of theory.

IR: 1760 cm$^{-1}$ (3-one), 1295, 870 and 815 cm$^{-1}$ (tetrahydropyranyl ether)

(1e)
(1S,3RS,5R,6R,7R)-6-[(E)-(3S,4S)-2-Bromo-3-(tetrahydropyran-2-yloxy)-4-methylnon-1-en-6-ynyl]-7-(tetrahydropyran-2-yloxy)-2-oxabicyclo[3.3.0]octan-3-ol At −70° C., 3.28 ml of a 20% strength solution of diisobutyl aluminum hydride in toluene is added dropwise to a solution of 984 mg of the compound obtained according to the above example in 23 ml of absolute toluene. After 30 minutes, excess hydride is decomposed by adding dropwise 0.18 ml of 2-propanol. The cooling bath is removed, the batch is mixed with 1.64 ml of water, and stirred until it can be suctioned off from the aluminum compounds. The mixture is rinsed with dichloromethane and the filtrate concentrated under vacuum. The desired compound remains as the residue in a quantitative yield.

IR: 3400 cm$^{-1}$ (OH), 1295, 870 and 815 cm$^{-1}$ (tetrahydropyranyl ether)

(1f)
14-Bromo-16β,20-dimethyl-18,18,19,19-tetradehydro-PGF$_{2\alpha}$ 11,15-Bis(tetrahydropyranyl ether)

At 0° under an argon atmosphere, 25.9 ml of a 1.18-molar butyllithium solution in hexane is added drop by drop to a mixture of 6.38 ml of hexamethyldisilazane and 22 ml of anhydrous tetrahydrofuran. After 30 minutes, this solution is then added dropwise to a suspension of 6.75 g of carboxybutyltriphenylphosphonium bromide in 66 ml of anhydrous tetrahydrofuran. The salt is dissolved with formation of ylide. Once solution is complete, a solution of 1.116 g of the lactol obtained in accordance with the above example in 18 ml of anhydrous tetrahydrofuran is added dropwise without delay, and then the mixture is heated for 90 minutes to 40°–45° C. Then the mixture is poured into 1 liter of ice-cold ammonium chloride solution, acidified by adding 10% strength citric acid solution to pH 4.5, and extracted four times with ether. The organic extract is extracted four times with respectively 5 ml of 1N sodium hydroxide solution and once with 5 ml of water. The combined alkaline extracts are again acidified by adding 10% strength citric acid solution and once again extracted four times with ether. This extract is dried with magnesium sulfate. The residue obtained after filtering off from the drying agent and evaporation of the solvent is further reacted as a crude product.

(1g)
14-Bromo-16β,20-dimethyl-18,18,19,19-tetradehydro-PGF$_{2\alpha}$ Methyl Ester 11,15-Bis(tetrahydropyranyl ether)

The crude product obtained in the preceding stage is dissolved in 22 ml of dichloromethane, cooled to 0° C., and combined with excess ethereal diazomethane solution. After 10 minutes, the excess diazomethane is decomposed by adding a small amount of acetic acid. The residue obtained after evaporation of the solvent is purified by chromatography on silica gel with a hexane-/acetone system. Yield: 976 g of the desired product, corresponding to 83.6% based on the lactol utilized in the preceding stage.

IR: 3450 cm$^{-1}$ (OH), 1730 cm$^{-1}$ (methyl ester)

(1h)
5-Iodo-14-bromo-16β,20-dimethyl-18,18,19,19-tetradehydro-PGI$_1$ Methyl Ester 11,15-Bis(tetrahydropyranyl ether)

A solution of 1.87 g of sodium bicarbonate in 31.5 ml of water is added to a solution of 952 mg of the methyl ester obtained according to the preceding example in 17.8 ml of ether. Under vigorous agitation, the mixture is cooled to 0° and a solution of 0.79 g of iodine in 27 ml of ether is added dropwise within 30 minutes. The mixture is stirred for another 4 hours under cooling. Then the phases are separated in a separating funnel. The ether phase is washed once with 5% sodium thiosulfate solution and twice with water. After drying with magnesium sulfate and filtration, the solvent is evaporated. The residue is purified by chromatography on silica gel with a hexane/ethyl acetate system, thus obtaining 1,061 mg of the desired compound, corresponding to 93.1% of theory.

IR: 1730 cm$^{-1}$ (methyl ester), 1295, 870 and 815 cm$^{-1}$ (tetrahydropyranyl ether)

(1i)
16β,20-Dimethyl-13,14,18,18,19,19-hexadehydro-PGI$_2$ 11,15-Bis(tetrahydropyranyl ether)

300 mg of the compound obtained in the preceding stage is dissolved in a mixture of 3.84 ml of anhydrous dimethyl sulfoxide and 1.61 ml of anhydrous tetrahydrofuran. Under an argon atmosphere, 220 mg of potassium tert-butylate is added and the mixture stirred for 2 hours at room temperature. Then the mixture is poured into 50 ml of ice/water, the clear solution is acidified to pH 6 with 10% strength citric acid solution and quickly extracted three times with ether. The extract is dried over magnesium sulfate with addition of several drops of triethylamine. After filtration, the drying agent is rinsed with ether/methanol 1:1. The filtrate is concentrated under vacuum and the remaining residue further processed in the form of the crude product.

(1j)
7-Oxo-16β,20-dimethyl-13,14,18,18,19,19-hexadehydro-PGI$_2$ 11,15-Bis(tetrahydropyranyl ether)

159 mg of crude product from the preceding stage is dissolved in 6 ml of anhydrous dioxane, 0.1 ml of hexamethyldisilazane and 27 mg of freshly sublimed selenium dioxide are added, and the mixture is heated to a bath temperature of 100° under an argon atmosphere and with agitation. After 15 minutes, 4 ml of absolute tertbutanol is added. After a total of 2 hours, the mixture is allowed to cool down to room temperature, combined with ice water, and extracted alternatingly twice each time with ether and ethyl acetate, respectively. The combined extracts are dried with magnesium sulfate. The residue remaining after filtration and evaporation of the solvent is purified by preparative layer chromatography, thus obtaining, after two purifying steps, 19.7 mg of the 7-keto compound (27.5% of theory).

IR: 1740 cm$^{-1}$ (acid), 1710 cm$^{-1}$ (ketone), 1650 cm$^{-1}$ ($\Delta^{5,6}$)

As the more polar component, 31.1 mg of 5-oxo-16β,20-dimethyl-6,7-13,4-bis(didehydro)-18,18,19,19-tetradehydro-PGI$^1$ 11,15-bis(tetrahydropyranyl ether) can be obtained (37.4% of theory).

IR: 1740 cm$^{-1}$ (acid), 1710 cm$^{-1}$ (ketone), 1615 cm$^{-1}$ ($\Delta^{6,7}$)

(1k)
(16S)-7-Oxo-16β,20-dimethyl-13,14,18,18,19,19-hexadehydro-PGI$_2$ 38 mg of the bis-tetrahydropyranyl ether from the foregoing example is stirred for 24 hours with 3.8 ml of a mixture of 65 parts of acetic acid, 35 parts of water and 10 parts of tetrahydrofuran at room temperature. After the volatile components have been evaporated under vacuum at room temperature, and distilling off twice with toluene, the residue is purified by preparative layer chromatography, thus obtaining 17.9 mg of the desired compound (67% of theory).

IR: 3400 cm$^{-1}$ (broad) (OH+acid), 1735 cm$^{-1}$ (acid), 1725 cm$^{-1}$ (7-ketone), 1650 cm$^{-1}$ ($\Delta^{5,6}$)

EXAMPLE 2

11,15-Bis(tetrahydropyran-2-yloxy)-16β,20-dimethyl-7-oxo-13,14,18,18,19,19-hexadehydro-3-oxa-PGI$_2$ tert-Butyl Ester 106 mg of 11,15-bis(tetrahydropyran-2-yloxy)-16β,20-dimethyl-13,14,18,18, 19,19-hexadehydro-3-oxa-PGI$_2$ tert-butyl ester from Example 2h is dissolved in 5 ml of anhydrous dioxane. After adding 29 mg of freshly sublimed selenium dioxide and 85 mg of hexamethyldisilazane, the mixture is heated to 95°-100° C. under argon for 75 minutes. Then the mixture is allowed to cool, combined with ice water, and extracted in alternation in each case twice with ether and ethyl acetate. The combined extracts are washed twice with water, dried with magnesium sulfate, and after filtration freed of the solvent under vacuum. The thus-obtained residue is purified twice by preparative layer chromatography, thus yielding 26 mg of still contaminated title compound.

IR: 1730 cm$^{-1}$ (ester+7-oxo), 1670 cm$^{-1}$ (5-ene)

Additionally, there is isolated 8 mg of the isomeric compound, 11,15-bis(tetrahydropyran-2-yloxy)-16β,20-dimethyl-5-oxo-13,14,18,18,19,19-hexadehydro-3-oxa-PGI$_2$ tert-butyl ester.

The starting material for Example 2 was prepared as follows:

(2a)
14-Bromo-11,15-bis(tetrahydropyran-2-yloxy)-16β,20-dimethyl-18,18,19,19-tetradehydro-2,3,4-trisnor-PGF$_{2\alpha}$ Ethyl Ester 650 mg of (1S,5R,6R,7R)-6-[(E)-(2RS,3S,4R)-2-bromo-4-methyl-3-(tetrahydropyran-2-yloxy)non-1-en- 6-ynyl]-7-(tetrahydropyran-2-yloxy)-2-oxabicyclo[3.3.-0]octan-3-one is dissolved in 24 ml of anhydrous toluene, 810 mg of (ethoxycarbonylmethylene)triphenylphosphorane is added, and the mixture is stirred under argon for 48 hours at room temperature. After the main quantity of toluene has been evaporated under reduced pressure, the mixture is introduced into a silica gel column. By elution with a gradient system of ethyl acetate and hexane, 704 mg of the title compound is obtained (96% of theory).

IR: 3450 cm$^{-1}$ (9-OH), 1720 cm$^{-1}$ (ethyl ester), 1640 cm$^{-1}$ (olefin)

(2b)
14-Bromo-9-tert-butyldimethylsilyloxy-11,15-bis(tetrahydropyran-2-yloxy)-16$\beta$,20-dimethyl-18,18,19,19-tetradehydro-2,3,4-trisnor-PGF$_{1\alpha}$ Ethyl Ester 703 mg of the compound according to (2a) is dissolved in 11.5 ml of anhydrous dimethylformamide, 196 mg of imidazole and 434 mg of tert-butyl dimethyl chlorosilane are added, and after agitation under argon for 2.5 hours, another 44 mg of imidazole and 109 mg of the chlorosilane are added, and the batch is allowed to stand overnight at room temperature. Then it is precipitated into ice-cold 10% strength ammonium chloride solution and extracted three times with ether. The combined organic extracts are washed twice with water, dried with magnesium sulfate, and the solvent is removed under vacuum. The residue is chromatographed on silica gel with an ethyl acetate/hexane system, yielding 750 mg of the title compound =89.9% of theory.

IR: 1720 cm$^{-1}$ (ethyl ester), 1640 cm$^{-1}$ (olefin), 840 cm$^{-1}$ +770 cm$^{-1}$ (silyl ether)

(2c)
14-Bromo-9-tert-butyldimethylsilyloxy-11,15-bis(tetrahydropyran-2-yloxy)-4-hydroxy-16$\beta$,20-dimethyl-18,18,19,19-tetradehydro-1,2,3-trisnor-PGF$_{2\alpha}$ 750 mg of the compound according to (2b) is dissolved in 13.3 ml of anhydrous toluene, argon is passed over the mixture and the latter cooled to 0° C. Dropwise, 3.75 ml of a 1.2-molar solution of diisobutyl aluminum hydride (in toluene) is added thereto. Then the mixture is stirred for 30 minutes at 0° C. Thereafter, 0.2 ml of 2-propanol and 1.88 ml of water are added dropwise, the cooling bath is removed, and agitation is conducted at room temperature until the reaction solution can be suctioned off from the precipitated aluminum compound. The product is rinsed with dichloromethane and the solvents are removed under vacuum. The residue (742 mg =100% of theory) is further processed without purification.

IR: 3420 cm$^{-1}$ (4-hydroxy), 830 cm$^{-1}$ +770 cm$^{-1}$ (silyl ether)

(2d)
9-tert-Butyldimethylsilyloxy-11,15-bis(tetrahydropyran-2-yloxy)-4-hydroxy-16$\beta$,20-dimethyl-13,14,18,18,19,19-hexadehydro-PGF$_{2\alpha}$ 742 mg of the compound according to (2c) is dissolved in a mixture of 5.4 ml of anhydrous dimethyl sulfoxide and 2.17 mg of anhydrous tetrahydrofuran. After passing argon over the reaction mixture, 243 mg of potassium tert-butylate is added and the mixture is stirred for 2 hours at room temperature. Then the mixture is combined with ice water, acidified with citric acid to pH 5, and extracted three times with ether:hexane =7:3 and twice with ether. The combined extracts are washed once with water, dried with magnesium sulfate, and after filtration freed of solvent under vacuum. The residue is purified by chromatography on silica gel with an ethyl acetate/hexane system, thus obtaining 367 mg (59% of theory) of the desired compound. By further elution, 98 mg of the 9-hydroxy compound is obtained.

IR: 3450 cm$^{-1}$ (4-hydroxy), 2250 cm$^{-1}$ (13,14-yne), 830+770 cm (silyl ether)

(2e)
9-tert-Butyldimethylsilyloxy-11,15-bis(tetrahydropyran-2-yloxy)-16$\beta$,20-dimethyl-13,14,18,18,19,19-hexadehydro-3-oxa-PGF$_{2\alpha}$ tert-Butyl Ester 366 mg of the compound according to (2d) is combined with 631 mg of bromoacetic acid tert-butyl ester, 1.52 ml of 50% strength potassium hydroxide solution, and 8.5 mg of tetrabutylammonium hydrogen sulfate, and vigorously agitated under an argon atmosphere for 2.5 hours. The mixture is diluted with 2.8 ml of water and acidified under cooling by dropwise addition of a solution of 1.35 g of citric acid monohydrate in 2.25 ml of water. Then the mixture is combined with ether and water, the phases are separated, and the aqueous phase is extracted twice with ether. The combined organic extracts are washed with semiconcentrated sodium chloride solution and dried with magnesium sulfate. The residue remaining after filtration and removal of the solvent by evaporation is chromatographed on silica gel with an ethyl acetate/hexane system, thus obtaining 392 mg of the title compound (90% of theory).

IR: 2260 cm$^{-1}$ (13,14-yne), 1760 cm$^{-1}$ (ester), 830+770 cm$^{-1}$ (silyl ether)

(2f)
11,15-Bis(tetrahydropyran-2-yloxy)-16$\beta$,20-dimethyl-13,14,18,18,19,19-hexadehydro-3-oxa-PGF$_{2\beta}$ tert-Butyl Ester 392 mg of the compound according to (2e) is dissolved in 5.4 ml of anhydrous tetrahydrofuran, 5.4 ml of a 1-molar solution of tetrabutylammonium fluoride in tetrahydrofuran is added, and the mixture is stirred under an argon atmosphere for 20 hours at room temperature. The mixture is combined with icecold 10% strength ammonium chloride solution and extracted twice with ether and once with ethyl acetate. The combined extracts are washed twice with water, dried over magnesium sulfate, filtered off, and evaporated under vacuum. The residue is chromatographed on silica gel. Elution with an acetone/hexane system yields 260 mg (79% of theory) of the title compound.

IR: 3500 cm$^{-1}$ (9-OH), 2250 cm$^{-1}$ (13,14-yne), 1760 cm$^{-1}$ (ester)

(2g)
11,15-Bis(tetrahydropyran-2-yloxy)-16$\beta$,20-dimethyl-5-iodo-13,14,18,18,19,19-hexadehydro-3-oxa-PGI$_1$ tert-Butyl Ester 260 mg of the compound according to (2f) is dissolved in 5.2 ml of ether and combined with a solution of 541 mg of sodium bicarbonate in 9.1 ml of water. Under argon and ice cooling, a solution of 230 mg of iodine in 7.8 ml of ether is added dropwise thereto Then the mixture is stirred for 4 hours while continuing cooling. The phases are then separated, the organic phase is washed with ice-cold 5% strength sodium thiosulfate solution and twice with water. After drying with magnesium sulfate, filtration and removal of solvent under vacuum, the residue is purified by chromatography on silica gel with hexane/ethyl acetate, thus obtaining 244 mg (77%) of the title compound and 60 mg of the starting compound (23%).

IR: 1760 cm$^{-1}$ (ester)

(2h)
11,15-Bis(tetrahydropyran-2-yloxy)-16β,20-dimethyl-13,14,18,18,19,19-hexadehydro-3-oxa-PGI$_2$ tert-Butyl Ester 244 mg of the compound according to (2g) is dissolved in 5.6 ml of anhydrous benzene, argon is passed thereover, 0.56 ml of diazabicycloundecene is added, and the mixture is agitated for 3 horus at 50°-60° C. After cooling to room temperature, the mixture is diluted with ethyl acetate and washed three times with water. The organic phase is dried with magnesium sulfate. After filtration, the solvent is removed under vacuum. The residue is further processed without purification.

EXAMPLE 3

7-Oxo-16β,20-dimethyl-13,14,18,18,19,19-hexadehydro-3-oxa-PGI$_2$ tert-Butyl Ester 44 mg of the compound according to Example 2 is stirred for 24 hours at room temperature with 4.4 ml of a mixture of 6.5 ml of acetic acid, 3.5 ml of water and 1 ml of tetrahydrofuran. The acetic acid is removed by distillation under vacuum at room temperature. After performing distillation twice with toluene, the residue is purified by preparative layer chromatography, thus obtaining 32 mg (75% of theory) of still slightly contaminated title compound IR: 3450 cm$^{-1}$ (OH), 1750 cm$^{-1}$ (ester+7-oxo), 1670 cm$^{-1}$ (5-ene)

EXAMPLE 4

7-Oxo-16β,20-dimethyl-13,14,18,18,19,19-hexadehydro-3-oxa-PGI$_2$ 32 mg of the compound according to Example 3 is dissolved in 1.25 ml of methanol, 0.1 ml of 10% strength lithium hydroxide solution is added, and the mixture is stirred under an argon atmosphere for 7 hours at room temperature. Then the mixture is neutralized by adding 29 mg of citric acid monohydrate, and the methanol is removed under vacuum at room temperature. The residue is triturated repeatedly with a dichloromethanemethanol mixture (7:3). The residue obtained after filtration and evaporation is purified by preparative layer chromatography, yielding 11.7 mg of pure title compound (42% of theory).

IR: 3400 cm$^{-1}$ (broad) (OH), 2250 cm$^{-1}$ (13,14-yne), 1740 cm$^-$(7-oxo), 1720 $^{-1}$ (acid)

We claim:

1. A 7-oxoprostacyclin compound of formula I

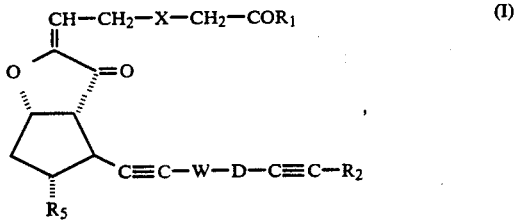

wherein
R$_1$ is OR$_3$ or NHR$_4$;
W is a hydroxymethylene or a

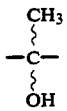

group, wherein the OH-group can be respectively esterified with a benzoyl or an alkanoic acid residue of 1-4 carbon atoms or etherified with a tetrahydropyranyl, tetrahydrofuranyl, (C$_1$-C$_4$-alkoxy)-C$_1$-C$_4$-alkyl or tri-(C$_1$-C$_4$-alkyl)-silyl residue, wherein the free or modified OH-group can be in the α- or β-position;
D is 2,3-propylene
R$_2$ is ethyl;
R$_3$ is hydrogen or C$_1$-C$_{10}$-alkyl optionally substituted by halogen, phenyl, C$_1$-C$_4$-alkoxy or C$_1$-C$_4$-dialkylamino;
R$_4$ is C$_1$-C$_{10}$-alkanoyl or C$_1$-C$_{10}$-alkanesulfonyl;
R$_5$ is a hydroxy group which can be esterified with an alkanoic acid residue of 1-4 carbon atoms or etherified with a tetrahydropyranyl, tetrahydrofuranyl, (C$_1$-C$_4$-alkoxy)-C$_1$-C$_4$-alkyl or tri-(C$_1$-C$_4$-alkyl)silyl residue;
X is an oxygen atom or the residue —CH$_2$—;
and, if R$_3$ is hydrogen, the salts thereof with physiologically compatible bases.

2. A compound of claim 1, wherein X is oxygen.
3. A compound of claim 1, wherein X is —CH$_2$—.
4. (16S)-13,14,18,18,19,19-Hexadehydro-16,20-dimethyl-7-oxo-PGI$_2$ a compound of claim 1.
5. (16S)-13,14,18,18,19,19-Hexadehydro-16,20-dimethyl-3-oxa-7-oxo-PGI$_2$a compound of claim 1.
6. A pharmaceutical composition comprising an effective amount of a compound of claim 1 and a pharmaceutically acceptable carrier.
7. A method of inhibiting thrombocyte aggregation, comprising administering a compound of claim 1.
8. A method of achieving an antihypertensive effect, comprising administering a compound of claim 1.

* * * * *